United States Patent [19]
Dietz et al.

[11] Patent Number: 6,022,926
[45] Date of Patent: Feb. 8, 2000

[54] ORGANOSILANES AND ORGANOPOLYSILOXANES CONTAINING 2-OXAZOLIDINONE GROUPS, THEIR USE AS SURFACE-ACTIVE SUBSTANCES AND THEIR USE FOR PREPARING ORGANOSILANES AND ORGANOPOLYSILOXANES CONTAINING AMINO OR CARBAMIDO GROUPS

[75] Inventors: Thomas Dietz; Christian Weitemeyer, both of Essen, Germany

[73] Assignee: Th. Goldschmidt Ag, Essen, Germany

[21] Appl. No.: 09/090,053

[22] Filed: Jun. 3, 1998

[30] Foreign Application Priority Data

Jun. 5, 1997 [DE] Germany .......................... 197 23 498

[51] Int. Cl.$^7$ ...................................... C08L 83/00
[52] U.S. Cl. .......................... 524/837; 428/447; 525/474; 556/420; 528/15; 528/26; 528/28
[58] Field of Search .................... 528/15, 26, 28; 556/420; 525/474; 524/837; 428/447

[56] References Cited

U.S. PATENT DOCUMENTS

| 4,680,410 | 7/1987 | Wang ........................................ 556/407 |
| 4,736,046 | 4/1988 | Chang ....................................... 556/414 |
| 5,496,478 | 3/1996 | Fost et al. . |
| 5,498,703 | 3/1996 | O'Lenick, Jr. . |
| 5,530,084 | 6/1996 | Ihara et al. . |

FOREIGN PATENT DOCUMENTS

| 0425209 B1 | 5/1991 | European Pat. Off. . |
| 0530811 A1 | 3/1993 | European Pat. Off. . |
| 7427702 | 7/1978 | France . |
| 2535023 | 3/1976 | Germany . |
| 2630107 | 1/1977 | Germany . |
| 2902129 | 7/1979 | Germany . |
| 19505892 C1 | 3/1996 | Germany . |
| 1478108 | 6/1977 | United Kingdom . |

OTHER PUBLICATIONS

Cancer & Chemotherapy, vol. 7, 1980, pp. 1942–1951.
Lourenco et al., Recent Advances in Chiral Separations, Plenum Press, New York, 1991, pp. 77–83.
The Chemical Society of Japan, vol. 11, 1985, pp. 2073–2076.
The Chemical Society of Japan, vol. 5, 1990, pp. 566–574.
Herweh et al., Tetrahedron Letters, No. 12, Pergamon Press, Great Britain, 1971, pp. 809–812.
Dyen et al., Chemistry of Epoxy Compounds, vol. 33, No. 1, Jan. 1968, pp. 379–384.
Huth et al., Liebigs Ann. Chem., 1979, pp. 56–62.
Dyen et al., "2–Oxazolidones," Fels Research Institute and Department of Chemistry, Temple University, Philadelphia, Jun. 22, 1966, pp. 197–246.

*Primary Examiner*—Melvyn I. Marquis
*Attorney, Agent, or Firm*—Frommer Lawrence & Haug LLP

[57] ABSTRACT

The invention relates to organosilanes and organopolysiloxanes which contain 2-oxazolidinone groups, where the oxazolidinone group is linked by the ring carbon atom C-4 or C-5 via a spacer to the silane or siloxane and the spacer is connected via a hydrolysis-stable Si—C bond to the silane or siloxane, their use as surface-active substances and also their use for preparing organosilanes and organopolysiloxanes containing amino or carbamido groups.

19 Claims, No Drawings

ORGANOSILANES AND ORGANOPOLYSILOXANES CONTAINING 2-OXAZOLIDINONE GROUPS, THEIR USE AS SURFACE-ACTIVE SUBSTANCES AND THEIR USE FOR PREPARING ORGANOSILANES AND ORGANOPOLYSILOXANES CONTAINING AMINO OR CARBAMIDO GROUPS

RELATED APPLICATIONS

This application claims priority to German application No. 197 23 498.4, filed Jun. 5, 1997, herein incorporated by reference.

BACKGROUND OF THE INVENTION

1. Field of the Invention

The invention relates to organosilanes and organopolysiloxanes which contain 2-oxazolidinone groups, where the oxazolidinone group is linked by the ring carbon atom C-4 or C-5 via a spacer to the silane or siloxane and the spacer is connected via a hydrolysis-stable Si—C bond to the silane or siloxane, to the use as surface-active substances and also to the use for preparing organosilanes and organopolysiloxanes containing amino or carbamido groups.

Oxazolidinone-functional silanes and polysiloxanes of the present invention have a high polarity and are easy to prepare. Because of their surface activity and their affinity to surfaces, the inventive compounds are used as additives in emulsion paints and surface coatings, for coating surfaces of pigments and fillers or in personal care and body cleansing products.

2. Description of the Related Art

To use polysiloxanes in polar media, it is necessary for polar groups to be built into the siloxane. Examples of siloxanes modified so as to be polar are polysiloxanes containing saccharide groups (U.S. Pat. No. 5,498,703), carbonate groups (DE-A-195 05 892), imidazoline groups (U.S. Pat. No. 5,496,478) and phosphate groups (U.S. Pat. No. 5,530,084). The compounds of the present invention represent a new class of organomodified polysiloxanes having particular properties.

There are many methods of preparing 2-oxazolidinones and these methods are described in the review article by M. E. Dyen and D. Swern (Chem. Rev., 67, 1967, 197–246). One method starts from epoxides which are reacted with nitrogen-containing reagents such as urea, alkyl carbamates or organic isocyanates. J. E. Herweh and W. J. Kauffman (Tetrahedron Letters, 12, 1971, 809–812) describe the lithium bromide-catalyzed reaction of epoxides with organic isocyanates in hydrocarbons as solvents to give N-substituted oxazolidinones. M. E. Dyen and D. Swern (J. Org. Chem., 33, 1968, 379–384) prepare N-unsubstituted oxazolidinones by the reaction of epoxides with potassium cyanate in dimethylformamide in the presence of tetraethylammonium bromide as catalyst. K. Kamagata (Nippon Kagaku Kaishi, 11, 1985, 2073–2076) isolated 5-(phenoxymethyl)-2-oxazolidinone from the reaction of phenyl glycidyl ether with isocyanuric acid in the presence of 2-methylimidazole.

DE-A-25 35 023 claims 5-(aryloxymethyl)-2-oxazolidinones, a process for their preparation from the corresponding epoxides using urea, as well as their use as medicaments. A. Huth and F. Neubauer (Liebigs Ann. Chem. 1979, 56–62) found that the yields of the reaction with urea are increased if dimethylformamide is used as solvent.

EP-B-0 425 209 describes the synthesis of N-naphthyl-substituted oxazolidinones from epoxides using N-naphthyl carbamates, while DE-A-26 30 107, GB-A-1 478 108, FR-B-2 281 114 and DE-A-29 02 129 describe the synthesis of N-unsubstituted oxazolidinones from epoxides using alkyl carbamates such as ethyl carbamate (urethane). EP-A-0 530 811 claims 5-(alkoxymethyl)- or 5-(alkenyloxymethyl)-2-oxazolidinones as well as a process for their preparation in which the corresponding epoxide is heated with a carbamate at temperatures above 150° C. in the absence of solvent using a combination of a tertiary amine with a tin compound as catalyst.

Although the literature describes an organotrimethoxysilane (Recent Adv. Chiral Sep., [Proc. Chromatogr. Soc. Int. Symp. Chiral Sep.], 2nd (1990), Meeting Date 1989, 77–83. Editors: D. Stevenson, I. D. Wilson, Publisher: Plenum, New York, N.Y.) and also a monofunctional organodisiloxane (Nippon Kagaku Kaishi, 5, 1990, 566–574 and Gan to Kagaku Ryoko, 7, 1980, 1942–1951) which contains an oxazolidinone group, in both those compounds the ring nitrogen bears a benzyl or phenyl substituent. There are no known oxazolidinone-functional organosilanes or organosiloxanes where the oxazolidinone ring bears a hydrogen or short-chain alkyl radical on the nitrogen. The absence of aromatic substituents on the nitrogen allows for the retention of the polar character of the oxazolidinone group thereby providing the compounds, in particular the polysiloxanes which are nonpolar by nature, a high compatibility with polar media.

A further advantage of the polysiloxanes of the invention compared to the known monofunctional disiloxane is that the ratio of (polar) oxazolidinone and (nonpolar) siloxane groups can be set to any desired value and can thus be tailored to the respective application.

OBJECT OF THE INVENTION

Surprisingly, it has now been found that organosilanes and organopolysiloxanes compounds which contain 5-membered cyclic urethane groups (2-oxazolidinone groups) display a high compatibility in polar media. Additionally, the inventive organosilanes and organopolysiloxanes can easily be prepared by simple methods. Furthermore, the inventive organosilanes and organopolysiloxanes can be used as intermediates to form amino- or carbamido-functional silanes or polysiloxanes.

SUMMARY OF THE INVENTION

The invention accordingly provides polysiloxanes containing 2-oxazolidinone groups and having the average formula

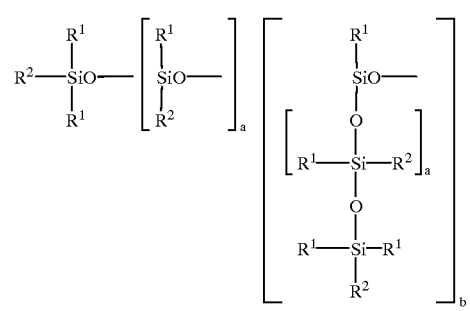

-continued

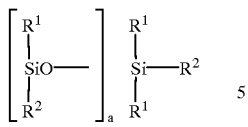

where the radicals $R^1$ are identical or different and are alkyl radicals having from 1 to 4 carbon atoms or phenyl radicals, but at least 90% of the radicals $R^1$ are methyl radicals, $R^2$ can be as defined for the radicals $R^1$, but at least one radical $R^2$ is a radical of the formulae

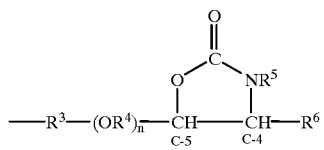

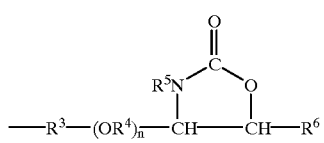

where $R^3$ is a branched or unbranched alkylene radical having from 1 to 20 carbon atoms and $R^4$ are identical or different alkylene radicals having from 1 to 4 carbon atoms, $R^5$ is H or an alkyl radical having from 1 to 8 carbon atoms, $R^6$ is H or an alkyl radical having from 1 to 4 carbon atoms or an alkylene radical which together with $R^3$ forms a ring and n is from 0 to 20, a is from 0 to 1,000, b is from 0 to 10.

The present invention further provides organosilanes containing 2-oxazolidinone groups and having the formula

where the radicals $R^8$ are identical or different and are alkyl radicals having from 1 to 4 carbon atoms, $R^2$ is a radical of the above-mentioned formulae and m is from 0 to 3.

DESCRIPTION OF THE PREFERRED EMBODIMENTS

Examples of organosilanes or organopolysiloxanes which are particularly preferred are those where $R^2$ (when $R^2 \neq R^1$) is

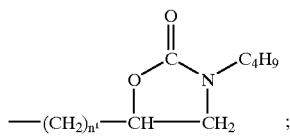

-continued

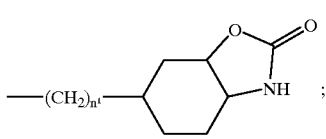

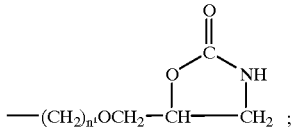

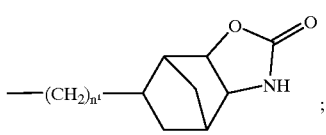

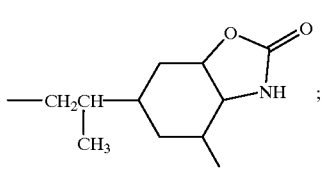

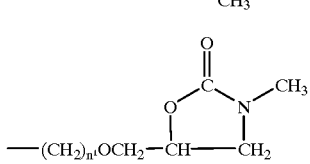

As examples of the novel silanes and polysiloxanes containing oxazolidinone groups are:

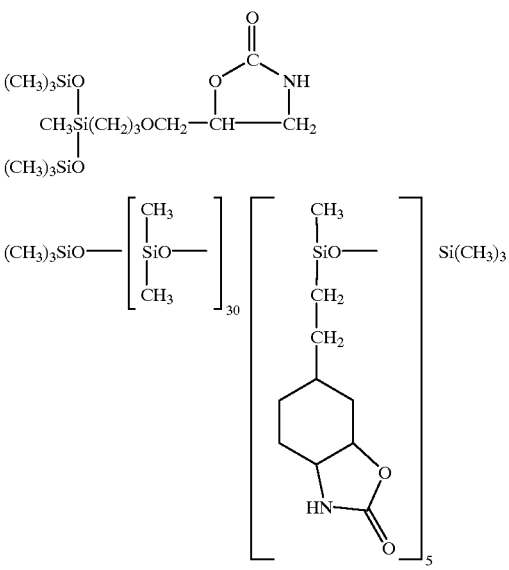

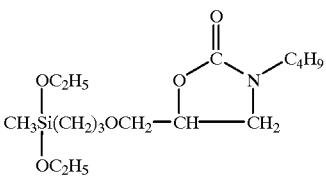

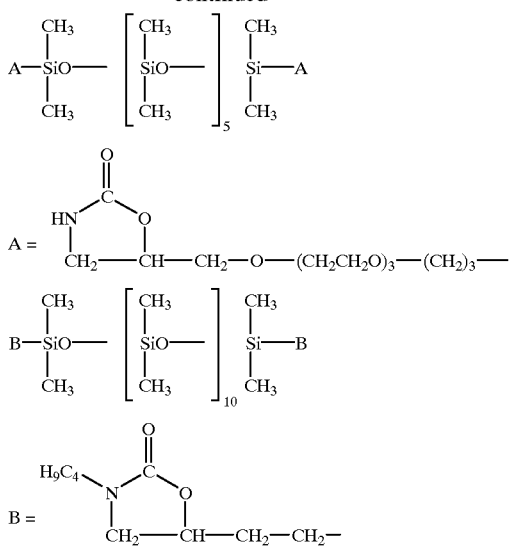

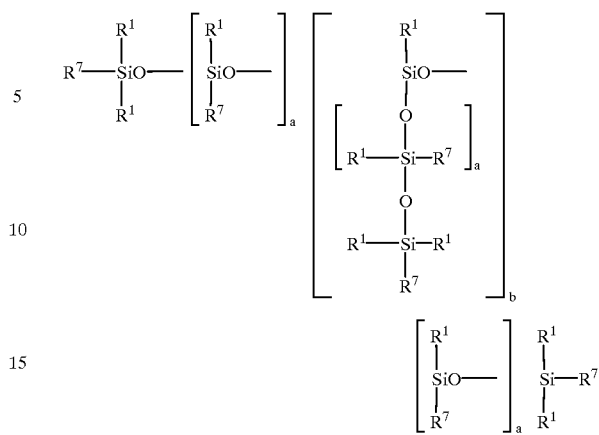

where
R⁷ can be $R^1$, but at least one radical $R^7$ is a radical of the formula

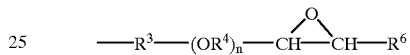

and the remaining radicals and indices are as defined above, which are reacted with a nitrogen-containing reagent.

The organosilanes and organopolysiloxanes of the present invention are prepared by various methods. One method is the hydrosilylation of oxazolidinones containing terminal C—C multiple bonds by means of a hydrogensilane or organohydrogenpolysiloxane. Oxazolidinone-functional mono-, di- or trialkoxysilanes are then converted into a polysiloxane by hydrolysis and equilibrating condensation. Preference is given to a process in which an epoxy-functional silane or polysiloxane is used as starting material. This is because a fundamental problem in the preparation of polysiloxanes modified so as to polar is presented by the great polarity difference between the (nonpolar) siloxane radical and the (polar) organic radical. This problem occurs particularly when a polar compound containing C—C multiple bonds is added to an organohydrogensiloxane in a hydrosilylation reaction. Because of the incompatibility of the reactants, relatively large amounts of solvent are necessary. This results in a relatively long reaction time and relatively drastic reaction conditions, both of which have an adverse effect on the purity of the products. It is also possible for absolutely no reaction to occur or only a low conversion of product to be observed. A further disadvantage of the direct hydrosilylation of oxazolidinones containing C—C multiple bonds is that the oxazolidinones, based on the organohydrogensiloxane, must be present in excess in order to obtain virtually complete conversion. In general, this excess cannot be removed by distillation. Therefore, the oxazolidinone remains in the product where it may have an adverse effect on the desired properties of the oxazolidinone-functional siloxane.

Surprisingly, it has been discovered that epoxy-functional polysiloxanes can be reacted with a nitrogen-containing reagent at temperatures of about 150° C. to form oxazolidinone-functional polysiloxanes without degradation reactions of the siloxane. The advantage of this preferred process, which is described in the examples, is that epoxy-functional organopolysiloxanes are known in the prior art and are commercially available. It is also possible to start from organopolysiloxanes which, apart from the epoxy-functional radicals, also bear other organic radicals, e.g. polyether or long-chain alkyl radicals.

Accordingly, starting materials used are compounds of the average formula

The reaction of epoxides with various nitrogen-containing reagents to form 2-oxazolidinones is described in the literature. Suitable reagents are urea and its derivatives, N-substituted and N-unsubstituted alkyl carbamates, cyanamide, cyanuric acid, inorganic cyanates and organic isocyanates. However, preference is given to urea, N-unsubstituted alkyl carbamates and organic isocyanates. The reaction is carried out in the presence or absence of a catalyst, but preferably in the presence of a catalyst. Catalysts used in the process are Lewis acids, amine bases, organometallic compounds, transition metal compounds and also alkali metal salts, alkaline earth metal salts or ammonium salts. For the reaction with epoxy-functional siloxanes, preference is given to those catalysts which have a high catalytic activity and at the same time fulfill the condition that they do not induce any degradation reactions on the siloxane framework. Particularly suitable catalysts are transition metal compounds such as alkyl titanates, e.g. butyl titanate, or organotin compounds, e.g. dibutyltin dilaurate, and also tertiary amines, e.g. triethylamine. A combination of a tertiary amine and an organotin compound, as described in EP-A-0 530 811, has been found to be particularly useful.

The reaction can be carried out in the presence or absence of a solvent. Suitable solvents are polar, high-boiling solvents such as dimethylformamide or ethylene glycol dimethyl ether. When using a solvent, it is particularly advantageous to employ a process in which an alcohol which simultaneously serves as solvent is reacted with urea in the presence of a suitable catalyst to form the corresponding carbamate which is reacted in situ or in a second stage. In both cases in the same reaction vessel, with the epoxy-functional siloxane to give the oxazolidinone-functional siloxane. The advantage of this procedure is, in particular, that urea is cheaper and more acceptable from a health point of view than certain alkyl carbamates. For example, ethyl carbamate is classified as a carcinogen. Examples of suitable alcohols are butanol, amyl alcohol, ethylene glycol monomethyl ether, methoxyisopropanol and dipropylene glycol monomethyl ether.

In the preferred process, the reactions are usually carried out at atmospheric pressure and temperatures of about 0 to about 220° C., preferably about 70 to about 160° C. The nitrogen-containing reagent is used in ratios of about 0.5 to about 2.5 mol, based on the epoxy function, but preference is given to about 1.0 mol. The amount of catalyst is about 0.1 to about 5% by weight, based on silane or siloxane reagent mixture used, preferably about 0.5 to about 3.0% by weight. If a solvent is used, its proportion in the total mixture is usually about 30 to about 70% by weight. The reaction is carried out to complete conversion of the epoxide, which can be determined by NMR or IR spectroscopy. Subsequently, the solvent used or volatile compounds formed during the reaction, for example ethanol which is formed from ethyl carbamate, can be distilled off. In the case of polysiloxanes, it is possible to leave solvent in the product since this ensures the flowability of the product.

Epoxysiloxanes in which the epoxy-functional radicals are linked via SiC bonds to the Si atoms of the siloxane are obtained in a manner known per se by adding epoxyalkenes or epoxyalkene ethers which have a terminal double bond accessible to hydrosilylation onto siloxanes containing SiH groups in the presence of hydrosilylation catalysts. Suitable, commercially available epoxyalkenes or epoxyalkene ethers are, for example, limonene oxide, allyl glycidyl ether, vinylcyclohexene oxide and 3,4-epoxy-1-butene.

The invention further provides for the use of oxazolidinone-functional silanes or polysiloxanes as intermediates for preparing silanes or polysiloxanes containing amino or carbamido groups. An overview of possible reactions of 2-oxazolidinones is given in the review article by M. E. Dyen and D. Swern (Chem. Rev., 67, 1967, 197–246).

to suppress the reaction of the product with as yet unreacted epoxide. Particular in the case of comb-like polysiloxanes, this secondary reaction can lead to crosslinking leading to gel-like products. The advantage of the two-stage synthesis described herein is that the oxazolidinone-functional siloxanes can be prepared without a secondary reaction and can then be reacted to set free the amino(hydroxy)-functional siloxanes.

Nucleophilic ring opening of the oxazolidinone ring by means of nitrogen nucleophiles such as ammonia, hydrazine or amines gives a 2-hydroxyalkylurea group. However, other nucleophiles are also suitable in principle for derivative formation.

Oxazolidinones are converted into N-substituted imidazoles by reaction with organic isocyanates.

The pyrolysis of oxazolidinones forms aziridines or their polymerization products. Thus, oxazolidinone-functional polysiloxanes are basically suitable for homopolymerization to form silicone-containing polyimines or for copolymerization with other monomers, e.g. epoxides or lactones, which makes their use as reactive components in plastics production conceivable.

The present invention further provides for the use of the compounds of the invention as surface-active substances. An important factor is the functionality of the siloxane copolymers, i.e. the ratio of oxazolidinone to siloxane groups in the organopolysiloxanes to be used according to the invention. As the functionality of the copolymer is increased, the polar character of the material increases and the solubility in polar solvents rises. Examples of polar solvents are water, water-soluble organic solvents such as methanol, ethanol, isopropanol, acetone, dioxane,

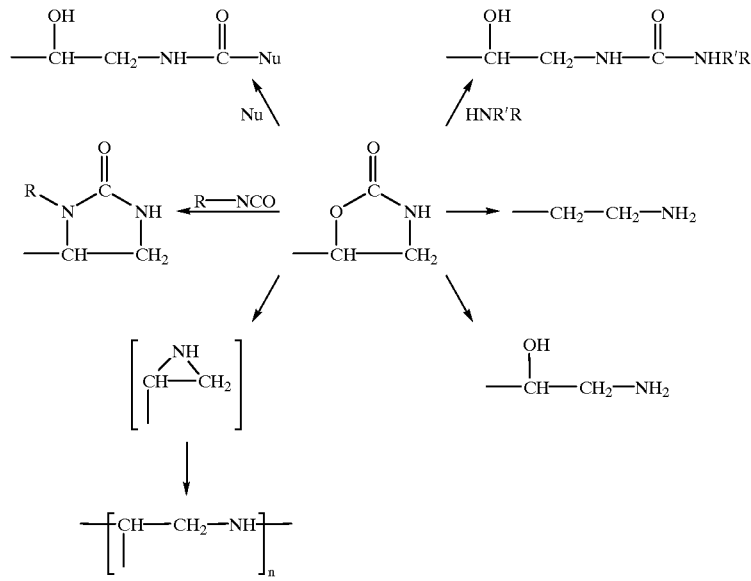

Oxazolidinones are converted into the corresponding 2-hydroxyamines by reduction or hydrolysis. Under certain conditions, deoxygenative reduction to amines is possible. This represents a novel route to aminosiloxanes, in particular to those having a long spacer between the amine function and the siloxane radical. Aminosiloxanes are widely used, for example as additives in cleaners and care products. Although aminohydroxy-functional siloxanes can theoretically be prepared from epoxy-functional siloxanes by reaction with ammonia, this requires a large excess of ammonia dimethylformamide, tetrahydrofuran, dimethyl sulfoxide and their mixtures.

Additionally, the polar behavior is influenced by the alkyl substituents which link the siloxane framework to the oxazolidinone groups. It has been discovered that the nonpolar character of the copolymer increases as the chain length of the alkyl radicals is increased. The introduction of polyether radicals additionally increases the solubility of the copolymer in polar systems.

From this, those skilled in the art will realize that the organopolysiloxanes according to the invention allow one to match the polarity of the organopolysiloxane with the chemical character of the solvent. For example, until solubility in water is achieved, and that the organopolysiloxanes to be used according to the invention are therefore particularly suitable for matching to the particular application.

The silanes and polysiloxanes which have been modified according to the invention can be used in a wide variety of applications. They are particularly suitable for use in aqueous media from which, owing to their surface activity and their affinity to surfaces, they develop their surface action. Depending on their structure, the silanes and polysiloxanes can be used in paints and varnishes where they improve the surface properties of the coating. They also can be employed as oil-in-water or water-in-oil emulsifiers in cosmetic preparations where they improve the foam. Examples of such cosmetic preparations are those used for cleaning skin and hair, for conditioning the hair, or for making the skin feel pleasant. Naturally, the polysiloxanes modified according to the invention are frequently used together with surfactants and other additives for influencing the properties of the surface.

All formulations mentioned can further comprise the customary additives. Examples of such agents include wetting agents, surfactants or emulsifiers selected from the classes of anionic, cationic, zwitterionic, amphoteric or nonionic surface-active substances, such as fatty alcohol sulfates, fatty alcohol ether sulfates, alkylsulfonates, alkylbenzene sulfates, alkyl sulfosuccinates, quaternary ammonium salts, alkylbetaines, carboxamidoalkylbetaines, derivatives of monomeric or more highly condensed saccharides, ethoxylated fatty alcohols, fatty acid alkanolamides or ethoxylated fatty acid esters, thickeners such as kaolin, bentonite, fatty acids, higher fatty alcohols, starch, polyacrylic acid and its derivatives, cellulose derivatives, alginates, vaseline or paraffin oil.

Furthermore, use of the compounds of the invention as textile auxiliaries, as additives in polyurethane foam production or in the formulation of additive packages for fuels is also conceivable.

EXAMPLES

Example 1

209.7 g (0.1 mol) of a polydimethylsiloxane of the formula $MD_{20}D^H_{7.5}M$ (formula 1) having lateral SiH functions and a mean total chain length of N=29.5 are placed together with 50 ml of toluene and 14.2 mg (=20 ppm of Pt) of hexachloroplatinic acid $H_2PtCl_6$ in a 800 ml four-neck flask fitted with stirrer, dropping funnel, thermometer and reflux condenser and the mixture is heated while stirring to 110° C. At this temperature, 85.61 g (0.75 mol) of allyl glycidyl ether are added dropwise at such a rate that a temperature of 130° C. is not exceeded despite the exothermic reaction which occurs. After addition is complete, the reaction mixture is stirred for another 1–2 hours at 110° C. until monitoring of the conversion by means of the SiH value shows that all the allyl glycidyl ether has been added on in the hydrosilylation reaction. At a conversion of >99%, the reaction is stopped and the Pt catalyst residues are removed from the reaction mixture by filtration. Solvent and volatile by-products are removed by distillation in an oil pump vacuum.

28.9 g (0.01 mol on the basis of the epoxy groups) of the epoxysiloxane thus prepared (formula 2) are placed in a flask which is fitted with stirrer, thermometer and reflux condenser and has been flushed with nitrogen. 6.68 g (0.075 mol) of ethyl carbamate (urethane) are dissolved therein by stirring and after addition of 0.71 g (=2%) of dimethylbenzylamine and 1.06 g (=3%) of dibutyltin dilaurate as catalysts the mixture is heated while stirring to 150° C. Refluxing is observed at this temperature and has become quite gentle after 1 hour. By means of $^1$H-NMR spectroscopy, the conversion can be determined from the decrease in the epoxide group and the increase in the oxazolidinone group. The oxazolidone has as characteristic signal a multiplet at 4.7 ppm which can be assigned to the proton on C-5 of the oxazolidinone ring.

After 2 hours, the mixture is cooled to room temperature. Distilling off the ethanol formed during the reaction in an oil pump vacuum gives a yellow, viscous reaction product which has lateral oxazolidinone groups and, according to analytical results, corresponds to the expected mean composition $MD_{20}D^{oxazolidinone}_{7.5}M$ (formula 3). If the ethanol is left in the product, it flows more readily.

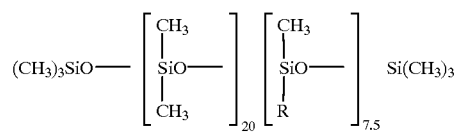

Formula 1

R = H

Formula 2

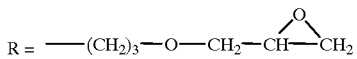

Formula 3

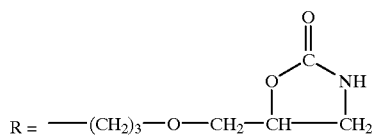

Example 2

In a flask which is fitted with stirrer, thermometer, dropping funnel and reflux condenser and has been flushed with nitrogen, 4.5 g (0.075 mol) of urea are melted at 135° C. while stirring. At this temperature, a solution of 28.9 g (0.01 mol on the basis of epoxy groups) of the epoxy siloxane prepared in Example 1 in 35 ml of dimethylformamide is added dropwise over a period of 1 hour and the mixture is stirred for another 7 hours at 135° C. Distilling off the solvent in an oil pump vacuum at 100° C. gives a yellow, viscous product which, according to analysis, is identical to the material prepared in Example 1.

Example 3

Using a method similar to that described in Example 1, an epoxysiloxane having the formula $M^{epoxide}D_{13}M^{epoxide}$ (formula 4) and a mean total chain length of N=15 is prepared by the platinum-catalyzed addition of 3,4-epoxy-1-butene onto a corresponding SiH-siloxane.

In a flask which is fitted with stirrer, thermometer, dropping funnel and reflux condenser and has been flushed with nitrogen, 12.0 g (0.2 mol) of urea and 35.3 g (0.4 mol) of amyl alcohol together with 0.5 g (=1%) of butyl titanate as catalyst are heated at 150° C. for 2 hours while stirring. Subsequently, 3.2 g (=2%) of dimethylbenzylamine and 4.8 g (=3%) of dibutyltin dilaurate as catalysts are added and 112.7 g (0.1 mol on the basis of the epoxy groups) of the epoxysiloxane prepared above (formula 4) are added dropwise at 150° C. over a period of 1 hour. The mixture is stirred for another 3 hours at this temperature and the solvent is subsequently distilled off at 100° C. in an oil pump vacuum. This gives a yellow reaction product which has terminal oxazolidinone groups and, according to analytical results, corresponds to the expected mean composition $M^{oxazolidinone}D_{13}M^{oxazolidinone}$ (formula 5).

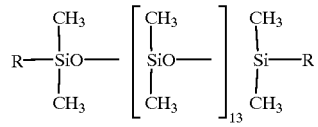

Formula 4

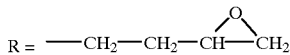

Formula 5

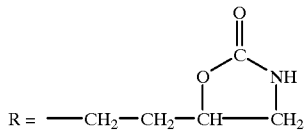

Example 4

A terminally and laterally modified epoxysiloxane of the formula $M^{epoxide}D_4D^{epoxide}_4M^{epoxide}$ (formula 6) is obtained by hydrosilylation of a polyoxyethylene polymer having the average formula $CH_2=CH—CH_2—(O—C_2H_4)_7—OH$ onto the corresponding SiH-siloxane and subsequent end capping of the primary hydroxy groups of the siloxane copolymer by means of epichlorohydrin. In a subsequent reaction, 323.1 g (0.1 mol on the basis of the epoxy groups) of this epoxysiloxane together with 36.1 g (0.6 mol) of urea, 91.3 g (1.2 mol) of ethylene glycol monomethyl ether plus 4.5 g (=1%) of isopropyl titanate, 9.0 g (=2%) of dimethylbenzylamine and 13.5 g (=3%) of dibutyltin dilaurate as catalysts are placed in a flask which is fitted with stirrer, thermometer and reflux condenser and has been flushed with nitrogen and the mixture is heated at 150° C. for 5 hours while stirring. Distilling off the solvent at 100° C. in an oil pump vacuum gives a yellow reaction product which has terminal and lateral oxazolidinone groups and, according to analytical results, corresponds to the expected mean composition $M^{oxazolidinone}D_4D^{oxazolidinone}_4M^{oxazolidinone}$ (formula 7)

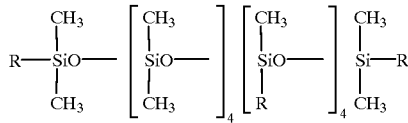

Formula 6

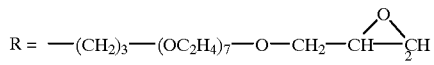

Formula 7

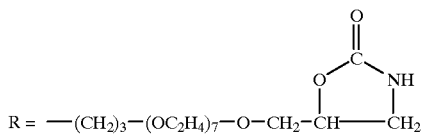

Example 5

24.8 g (0.1 mol) of commercially available glycidoxypropyl-methyldiethoxysilane (formula 8) are placed in a three-neck flask which is fitted with stirrer, thermometer and reflux condenser and has been flushed with nitrogen. 8.9 g (0.1 mol) of ethyl carbamate are dissolved therein by stirring and, after addition of 0.67 g (=2%) of dimethylbenzylamine and 1.01 g (=3%) of dibutyltin dilaurate as catalysts, are heated at 120° C. for 1 hour while stirring. Ethanol formed is subsequently distilled off under atmospheric pressure via a distillation attachment. This gives a yellow reaction product which, according to analytical results, has the expected structure (formula 9).

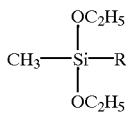

Formula 8

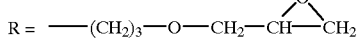

Formula 9

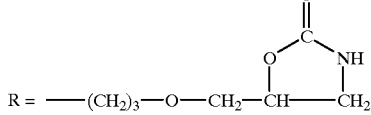

Example 6

In a flask which is fitted with stirrer, thermometer, dropping funnel and reflux condenser and has been flushed with nitrogen, a solution of 28.9 g (0.01 mol on the basis of the epoxy groups) of the epoxysiloxane prepared in Example 1 and 1.1 g (=3%) of lithium chloride in 60 ml of dimethylformamide is heated while stirring to 150° C. A solution of 7.4 g (0.075 mol) of butyl isocyanate in 15 ml of dimethylformamide is added dropwise over a period of 1 hour and the mixture is stirred for another 3 hours at 150° C. Distilling off the solvent at 100° C. in an oil pump vacuum gives a pale brown product which, according to analytical results, has the expected structure (formula 10).

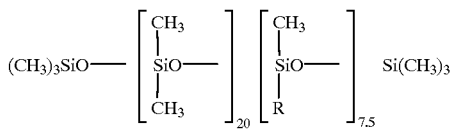

Formula 10

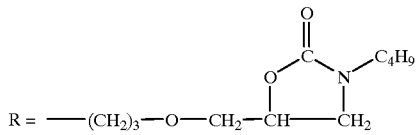

Use tests

To test the use properties of the oxazolidinone-functional polysiloxanes of the invention, the product from Example 1 is mixed, in each case in a concentration of 1%, with various solvent/water mixtures. The following table shows the results obtained in comparison with the starting material which is not according to the invention. It can be seen from the results that the oxazolidinone-functional polysiloxanes have a distinctly more polar character than the corresponding epoxy-functional siloxanes. In the case of a 3:1 mixing ratio of solvent to water, the oxazolidinone-functional siloxane in all cases gives a homogeneous solution, while the epoxy-functional siloxane in most to separation of an oily phase. cases leads to separation of an oily phase.

TABLE 1

Appearance of 1% strength solutions of an oxazolidinone-functional siloxane (M-D$_{20}$-D$^{oxazolidinone}$$_{7.5}$-M) in solvent/water mixtures (1:1) in comparison with solutions of the corresponding epoxy-functional siloxane

| Solvent in the 1:1 mixture with water | Appearance[1]) of 1% strength solutions of siloxane | |
|---|---|---|
| | oxazolidinone | epoxide |
| Isopropanol | 1 | 3 |
| Ethanol | 2 | 3 |
| Dioxane | 2 | 3 |
| Methanol | 3 | 3 |
| Acetone | 3 | 3 |
| Tetrahydrofuran | 3 | 3 |
| Ethylene glycol monomethyl ether | 3 | 3 |
| Propylene glycol | 3 | 3 |

[1])1 = clear solution
2 = turbid or opaque, but homogeneous
3 = precipitate or separation of an oily phase

TABLE 2

Appearance of 1% strength solutions of an oxazolidinone-functional siloxane (M-D$_{20}$-D$^{oxazolidinane}$$_{7.5}$-M) in solvent/water mixtures (3:1) in comparison with solutions of the corresponding epoxy-functional siloxane

| Solvent in the 3:1 mixture with water | Appearance[1]) of 1% strength solutions of siloxane | |
|---|---|---|
| | oxazolidinone | epoxide |
| Tetrahydrofuran | 1 | 2 |
| Isopropanol | 1 | 3 |
| Ethanol | 1 | 3 |
| Acetone | 1 | 3 |
| Ethylene glycol monomethyl ether | 2 | 2 |
| Dioxane | 2 | 2 |
| Methanol | 2 | 3 |
| Propylene glycol | 2 | 3 |

[1])1 = clear solution
2 = turbid or opaque, but homogeneous
3 = precipitate or separation of an oily phase The tables demonstrate that the modified organopolysiloxanes to be used according to the invention have the desired use properties.

The above description of the invention is intended to be illustrative and not limiting. Various changes or modifications in the embodiments described may occur to those skilled in the art. These can be made without departing from the scope and spirit of the invention.

We claim:

1. A polysiloxane containing 2-oxazolidinone groups and having the average formula

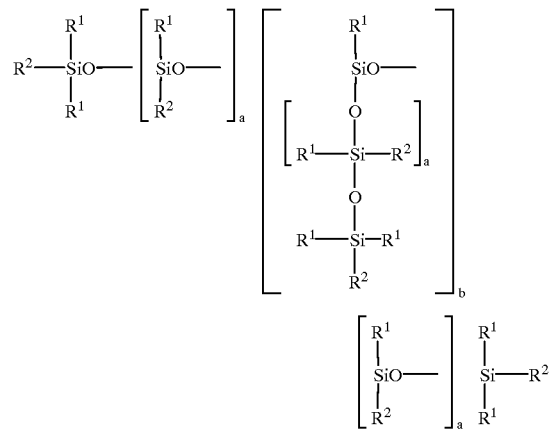

where the radicals $R^1$ are identical or different and are alkyl radicals having from 1 to 4 carbon atoms or phenyl radicals, wherein at least 90% of the radicals $R^1$ are methyl radicals, $R^2$ is as defined for the radicals $R^1$, where at least one radical $R^2$ is a radical of the formulae

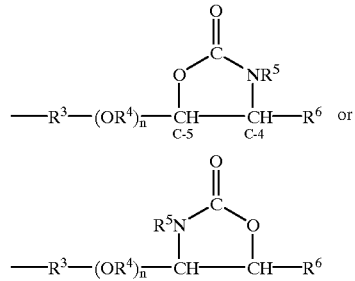

where $R^3$ is a branched or unbranched alkylene radical having from 1 to 20 carbon atoms and $R^4$ are identical or different alkylene radicals having from 1 to 4 carbon atoms, $R^5$ is H or an alkyl radical having from 1 to 8 carbon atoms, $R^6$ is H or an alkyl radical having from 1 to 4 carbon atoms or an alkylene radical which together with $R^3$ forms a ring and n is from 0 to 20, a is from 0 to 1,000, b is from 0 to 10, or an organosilane containing 2-oxazolidinone groups and having the formula

where the radicals $R^8$ are identical or different and are alkyl radicals having from 1 to 4 carbon atoms, $R^2$ is a radical of the above-mentioned formulae and m is from 0 to 3.

2. An organopolysiloxane or organosilane as claimed in claim 1, selected from the group consisting of

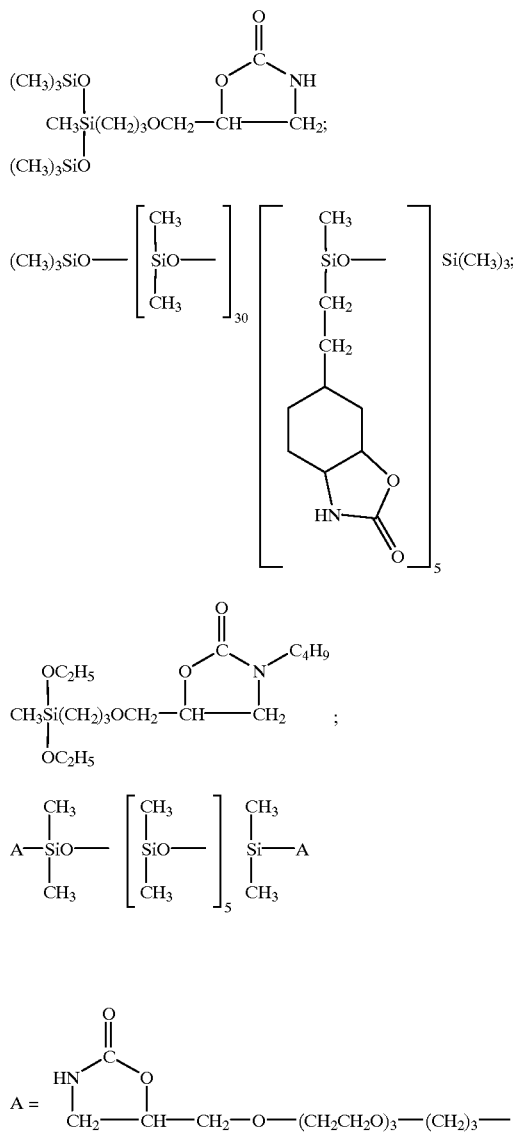

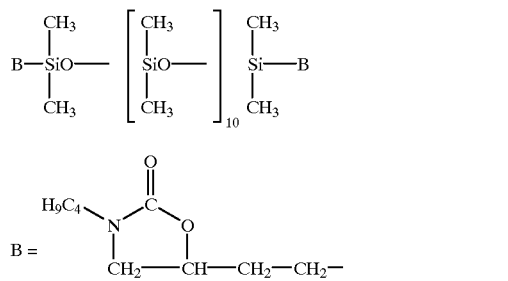

3. A process for preparing a 2-oxazolidinone polysiloxane according to claim 1 which comprise reacting an epoxy-functional polysiloxane of the formula

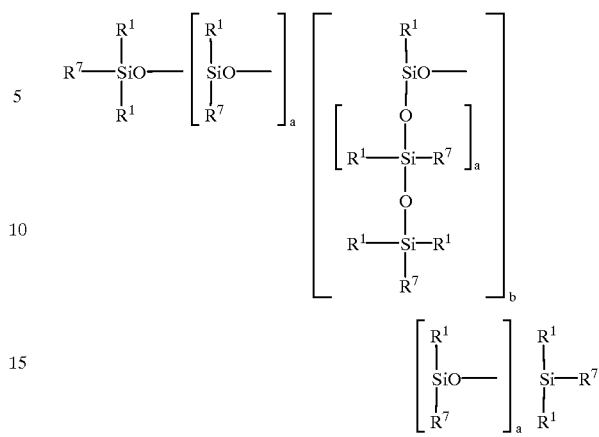

where $R^7$ can be $R^1$, but at least one radical $R^7$ is a radical of the formula

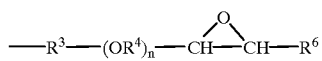

and the remaining radicals and indices are as defined in claim 1, with a nitrogen-containing reagent optionally in the presence of a solvent and a catalyst selected from the group consisting of a Lewis acid, an amine base, an organometallic compound, a transition metal compound, an alkali metal salt, an alkaline earth metal salt and an ammonium salt.

4. The process according to claim 3, wherein the nitrogen containing reagent is urea or a derivative thereof, N-substituted and N-unsubstituted alkyl carbamates, cyanamide, cyanuric acid, inorganic cyanates or organo isocyanates.

5. The process according to claim 3, wherein the reaction temperature is about 0 to about 220° C.

6. The process according to claim 3, wherein the reaction temperature is about 70 to about 160° C.

7. The process according to claim 3, wherein the amount of catalyst used is about 0.1 to about 5% by weight, based on the siloxane, and the catalyst is a transition metal compound, an organotin compound or a tertiary amine or mixture of a tertiary amine and an organotin compound.

8. A cosmetic formulation which comprises a polysiloxane or an organosilane according to claim 1.

9. The formulation according to claim 8 wherein the formulation is a skin or hair conditioner or a formulation for cleansing the skin or hair.

10. An oil-in-water or a water-in-oil emulsion which comprises a polysiloxane or an organosilane according to claim 1 as the emulsifier.

11. An emulsion paint or surface coating which comprises a polysiloxane or an organosilane according to claim 1.

12. A method for reducing the surface tension of an aqueous solution or for reducing the interfacial tension between two liquid or between a liquid and a solid which comprises adding a polysiloxane or organosilane according to claim 1.

13. In a method for preparing additive packets for fuels, the improvement which comprises adding a polysiloxane or organosilane as claimed in claim 1 to the pocket for fuels.

14. In a method for preparing polyurethane foams, the improvement which comprises adding a polysiloxane or organosilane as claimed in claim 1 to the process for preparing polyurethane foams.

15. In a method for preparing a textile, the improvement which comprises adding a polysiloxane or organosilane as claimed in claim 1 to the process for preparing a textile.

16. In a method for improving the surface qualities of an emulsion paint or surface coating the improvement which comprises adding a polysiloxane or organosilane as claimed in claim 1 to said paint or surface coating.

17. An organopolysiloxane or organosilane as claimed in claim 1, where $R^2$ does not equal $R^1$ and $R^2$ is selected from the group consisting of

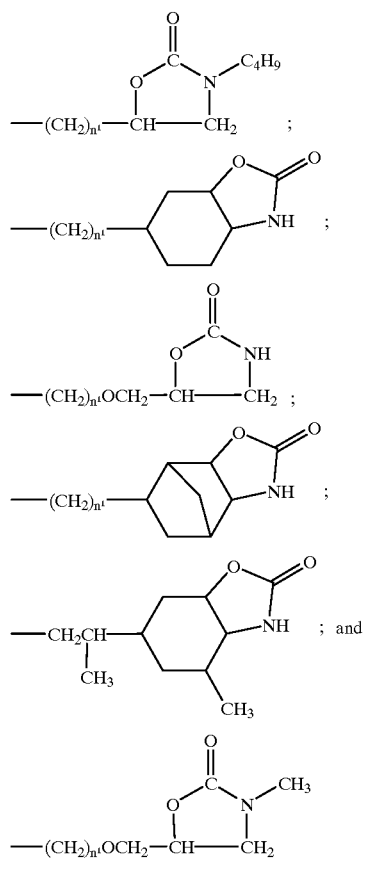

where $n^1$ is from 1 to 20.

18. An organopolysiloxane or organosilane as claimed in claim 1, where $R^2$ is selected from the group consisting of

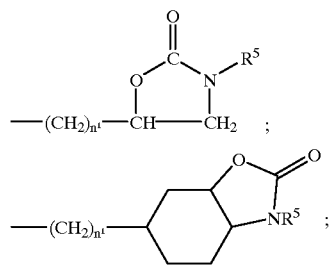

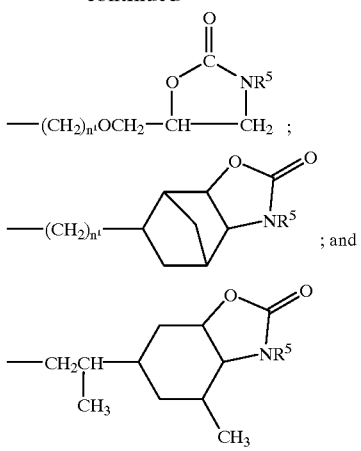

where $n^1$ is from 1 to 20, and $R^5$ is hydrogen or an alkyl radical having 1 to 8 carbon atoms.

19. An organopolysiloxane or organosilane as claimed in claim 1, wherein the compound is selected from the group consisting of

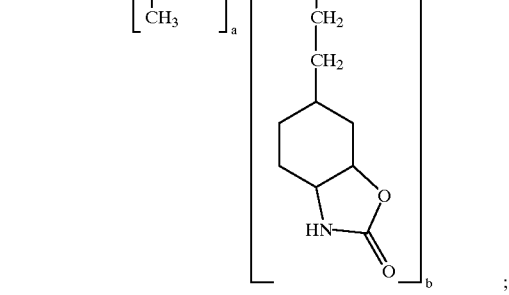

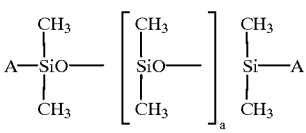

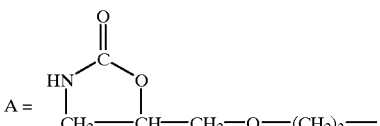

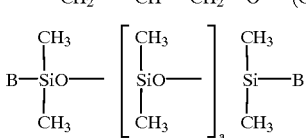

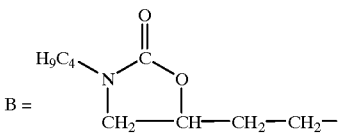

-continued
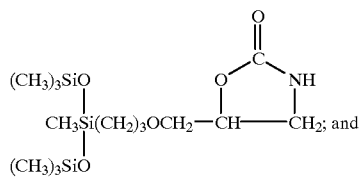; and
-continued
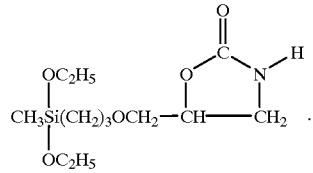.
* * * * *